United States Patent [19]

Barnikol et al.

[11] Patent Number: 4,775,514

[45] Date of Patent: Oct. 4, 1988

[54] LUMINESCENT LAYERS FOR USE IN APPARATUS FOR DETERMINING THE OXYGEN CONCENTRATION IN GASES AND THE LIKE

[76] Inventors: Wolfgang Barnikol, 6500 Mainz Lanzelhohl 66; Oswald Burkhard, Schillerstrabe 9, 6761 Kriegsfeld, both of Fed. Rep. of Germany

[21] Appl. No.: 854,901

[22] Filed: Apr. 23, 1986

Related U.S. Application Data

[63] Continuation-in-part of Ser. No. 617,916, Jun. 6, 1984, abandoned.

[30] Foreign Application Priority Data

Jun. 6, 1983 [DE] Fed. Rep. of Germany ....... 3320752

[51] Int. Cl.$^4$ ...................... G01N 21/64; G01N 31/22
[52] U.S. Cl. .................... 422/68; 250/458.1; 422/83; 422/55; 436/68; 436/136; 436/172
[58] Field of Search ........ 422/52, 55, 68, 83, 422/88, 91; 436/136, 138, 164, 172; 250/458.1, 459.1; 128/633, 634

[56] References Cited

U.S. PATENT DOCUMENTS

| | | | |
|---|---|---|---|
| 4,003,707 | 1/1977 | Lübbers et al. | 436/172 |
| 4,399,099 | 8/1983 | Buckles | 436/136 |
| 4,557,900 | 12/1985 | Heitzmann | 422/55 |
| 4,558,014 | 12/1985 | Hirschfeld et al. | 422/55 |
| 4,560,248 | 12/1985 | Cramp et al. | 128/633 |
| 4,577,109 | 3/1986 | Hirschfeld | 250/461.1 |
| 4,587,223 | 5/1986 | Soini et al. | 436/172 |
| 4,657,736 | 4/1987 | Marsoner et al. | 436/172 |

FOREIGN PATENT DOCUMENTS 2823318  11/1979  Fed. Rep. of Germany ........ 422/52

OTHER PUBLICATIONS

CRC Handbook of Chem. & Phys., 1970, pp. D106–D107.

Primary Examiner—Michael S. Marcus
Attorney, Agent, or Firm—Keil & Weinkauf

[57] ABSTRACT

A luminescent layer for use in apparatus for determining the oxygen concentration in gases, fluids and tissues by measuring the decrease in the light emission of a luminescent surface irradiated with an excitation light of a certain wavelength, where the luminescent dye forms a homogeneous mixture with the light-transparent layer substance, in which case the surface may also have a fine-grained structure.

10 Claims, No Drawings

LUMINESCENT LAYERS FOR USE IN APPARATUS FOR DETERMINING THE OXYGEN CONCENTRATION IN GASES AND THE LIKE

This application is a continuation-in-part of U.S. application Ser. No. 617,916, filed June 6, 1984, abandoned, which was copending with related application Ser. No. 445,960, which was filed on Dec. 1, 1982, the disclosures of which is incorporated in the present application. Application Ser. No. 445,960 was based on German Patent Application No. P 31 48 830.7.

The application is directed to improved luminescent layers for use in apparatus for determining the oxygen concentration in gases or the like. The oxygen concentration is found by measuring the decrease in luminescence of the layer caused by the sample to be analyzed.

In the related application, an apparatus is described for determining the oxygen concentration in gases, fluids and tissues by measuring the decrease in light emission of a luminescent surface irradiated with an excitation light of a certain wavelength, where said surface is formed by a single layer of densely packed particles having a diameter of less than 1 mm, preferably less than 0.1 mm. This surface consists of either the luminescent substance itself, or the luminescent substance is adsorbed on an inert substrate. In a further development, the sample and the measured layer are separated by an oxygen-transparent membrane.

It has now been found that good and useful measuring results can also be obtained when the luminescent dye is incorporated into a light transparent layer substance in such a way that a homogeneous mixture or dyeing of the layer substance is obtained.

In this case, the preparation is considerably simplified, as compared to the layers known from German Patent Application No. P 31 48 830.7, which is especially advantageous for industrial production.

The characteristics of the layer substance, which in all cases must be very oxygen-transparent, may be selected according to the intended usage. If, for example, a hydrophobic substance is used as the layer substance, measuring signals are obtained that are independent of the moisture content of the sample. For the preparation of the luminescent layers according to the invention, the following methods or their combinations may be used, among others:

1. The layer substance and the dye are dissolved together in a suitable solvent or a combination of solvents, and the solution will then be distributed on the substrate. The luminescent layer is obtained after the evaporation of the solvent.
2. The dye is melted into the layer substance. For this purpose, the layer substance and the dye are heated to above their melting points, and the liquified mass is thinly distributed on the substrate. The desired luminescent layer will form after cooling.
3. Monomers or oligomers are mixed with the dye, possibly while adding a suitable solvent, the mixture is distributed on substrate, and polymerization is started.

Silicone caoutchouc has proven to be an especially suitable layer substance.

All hydrophobic fluorescent dyes with an appropriate fluorescent life time can be used. Hydrophobic fluorescent dyes which have proven to be well suited are fluorescent yellow, pyrene, coronene, cyano derivatives of benzene and porphyrine.

Inasmuch as a surface of the luminescent layer is desired that is as large as possible, it is especially advantageous to apply this luminescent layer not to a plane substrate, such as a glass plate, but to use a substrate the surface of which is not smooth. Such a substrate is, for example, a plate layered with a fine-grained substance, such as silica gel. The grain size of the fine-grained substance should be smaller than 1 mm, preferably less than 0.1 mm.

It was also found that the thickness of the layer containing the luminescent dye has no influence on the measuring result so that in the case of the layer according to the invention, varying layer thicknesses caused by process tolerances are of no disadvantage.

EXAMPLE

A 40% solution of silicone caoutchouc in toluol (E 385, Wacker Chemie München, Federal Republic of Germany) was diluted at a ratio of 1:3 with toluol, and 30 µl of a solution of 10 mg (see above) in a 1 ml toluol were added to a 1.4 ml of this solution. 25 µl of this solution were then distributed on a small glass plate of a diameter of about 1 cm. In order to obtain a homogenous layer, during the drying, the liquid film was constantly distributed by means of a rod so that a formation of drops was avoided.

By means of such a layer, 90% response times of about 60 ms were obtained in the apparatus according to the German Patent Application No. 31.48 830.7. The $O_2$-sensitivity was satisfactory, and the signal was independent of the moisture content of the sample.

In a further experiment a 40% solution of silicone caoutchouc in toluol (E 385, Wacker Chemie, München, Federal Republic of Germany) was diluted at a ratio of 1:3 with toluol, and 30 µl of a solution of 50 mg pyrene in 10 ml toluol were added to 1.4 ml of silicone caoutchouc solution, 25 µl of this solution were then distributed on a small glass plate with a diameter of about 1 cm. In order to obtain a homogeneous layer during the drying, the liquid film was constantly distributed by means of a rod so that a formation of drops was avoided. With this layer there was observed a similar $O_2$ sensitivity of the fluorescence signal as with fluorescent yellow. Preliminary results indicate that the 90% response times are even lower than with fluorescent yellow.

In further experiments coronene was used as a fluorescent dye. The $O_2$-sensitive layer was made by the same procedure as outlined above, but 30 µl of a solution of 10 mg coronene in 10 ml toluol were added to the silicone caoutchouc solution. The layer obtained had similar properties considering fluorescence like the pyrene layer.

The fourth dye used, was 1-dimethyl-amino-2,6-dicyano-4-methyl-benzene (DDMB). 30 µl of a solution of 20 mg DDMB in 10 ml toluol were added to the silicone caoutchouc soluton and the $O_2$-sensitive layer was prepared in the same manner as outlined above. The DDMB layer had a satisfactory $O_2$ sensitivity, too, and the signal was independent of the moisture of the sample.

The above examples show that different dyes are well suited for an $O_2$-sensitive layer. These experimental results clearly demonstrate that many hydrophobic fluorescent dyes are applicable.

We claim:
1. A luminescent layer for use in apparatus for determining the oxygen concentration in gases, fluids and tissues by measuring the decrease of the luminescence in the light emission of a luminescent surface irradiated with an excitation light of a certain wavelength, wherein the luminescent layer consists essentially of an homogeneous mixture of a luminescent dye and an hydrophobic light transparent layer substance.

2. A luminescent layer according to claim 1, wherein silicone caoutchouc is used as the layer substance.

3. A luminescent layer according to claim 2, further including a substrate, said substrate having a fine grained surface for supporting said luminescent layer.

4. A luminescent layer according to claim 1, further including a substrate, said substrate having a fine-grained surface for supporting said luminescent layer.

5. A luminescent layer according to claim 4, wherein the grain size of the fine-grained surface is smaller than 1 mm.

6. A luminescent layer according to claim 1, wherein the luminescent dye is fluorescent yellow.

7. A luminescent layer according to claim 6, werein about 10 mg of fluorescent yellow is present to about 1.4 ml of layer solution.

8. A luminescent layer according to claim 1, wherein the luminescent dye is pyrene.

9. A luminescent layer according to claim 1, wherein the luminescent dye is coronene.

10. A luminescent layer according to claim 1, wherein the luminescent dye is a cyano derivative of benzene.

* * * * *